United States Patent [19]

Allen et al.

[11] 4,202,212
[45] May 13, 1980

[54] IN-LINE RESPIRATING PUMP

[75] Inventors: Richard T. Allen, Easton, Md.;
Rudolph H. Moyer, West Covina, Calif.; Donald J. Sibbett, Cucamonga, Calif.; Howard H. Anderson, Covina, Calif.; Glen R. Martner, Rosemead, Calif.; Don Willis, Garden Grove, Calif.

[73] Assignee: Geomet, Incorporated, Gaithersburg, Md.

[21] Appl. No.: 901,862

[22] Filed: May 1, 1978

[51] Int. Cl.² ............................................. G01N 1/14
[52] U.S. Cl. .................................... 73/421.5 R; 128/719; 128/730; 128/1 R; 73/28; 417/234; 55/270
[58] Field of Search ............... 128/24 R, 25 R, 33, 128/725–729, 719, 730, 774–782, 653–659, 717, 718, 28, 30, 30.2, 140 R, 145 R, 145.6, 145.7, DIG. 29, 185, 278, 1 R; 417/234; 422/83; 55/270; 73/421.5 R, 28; 272/99

[56] References Cited

U.S. PATENT DOCUMENTS

| | | | |
|---|---|---|---|
| 1,055,267 | 3/1913 | Gibson | 272/99 X |
| 3,097,639 | 7/1963 | Streimer | 128/2.08 |
| 3,366,060 | 1/1968 | Jennings | 417/234 |
| 3,410,059 | 11/1968 | Garnier | 73/421.5 X |
| 3,802,250 | 4/1974 | Garnier | 73/28 |
| 3,956,940 | 5/1976 | Guild | 73/421.5 X |

FOREIGN PATENT DOCUMENTS 1480160  9/1967  France ............................ 128/2 C

*Primary Examiner*—Henry J. Recla
*Attorney, Agent, or Firm*—David H. Semmes

[57] ABSTRACT

Device for sampling air in proportion to respiration, particularly the collection of air pollutants in proportion to the actual respiration of the wearer. The device includes a pump supported adjacent the thoracic cavity and activated by the expansion and contraction of the thoracic cavity during respiration, so as to draw air through an air sampling monitor.

8 Claims, 5 Drawing Figures

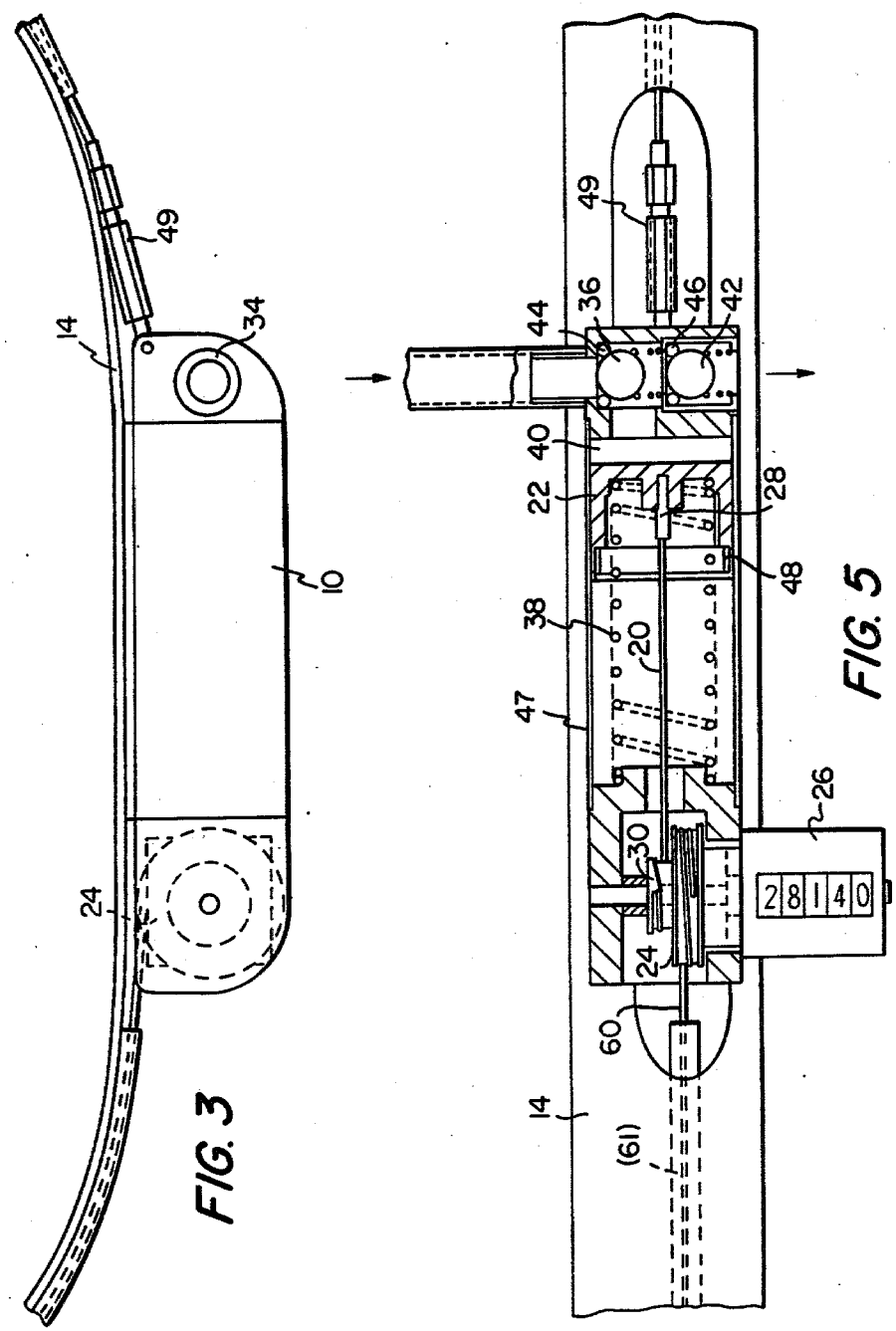

IN-LINE RESPIRATING PUMP

CROSS REFERENCES TO RELATED APPLICATIONS

Modification of the respirating pump apparatus are disclosed in Applicants' applications earlier filed entitled METHOD FOR SAMPLING AIR IN PROPORTION TO RESPIRATION (Ser. No. 901,654 filed May 1, 1978); FLOATING PISTON RESPIRATING PUMP (Ser. No. 901,653 filed May 1, 1978); and RESPIRATING PUMP (Ser. No. 901,861 filed May 1, 1978).

BACKGROUND OF THE INVENTION

Air pollution monitors, particularly respirating pumps adapted for support upon the thoracic cavity, so as to be activated during respiration. The pump includes an air pollution sampler, a counter of air volume inhaled and a digital readout, such that pollutants collected during a given period may be correlated with the quantity of air respired.

DESCRIPTION OF THE PRIOR ART

Being submitted separately under the provisions of 37 C.F.R. 1.97.

SUMMARY OF THE INVENTION

Device for sampling air pollution in proportion to respiration, comprising supporting an air sampling monitor adjacent the mouth of a respirant human, pumping air through the sampler, according as the respirant's thoracic cavity expands and contracts, and gauging the amount of pollutants collected within the air sampling monitor as the amount of pollutants actually inhaled by the respirant during a given period. The device includes an in-line respirating pump attachable to an expandable belt, encircling the thoracic cavity, as the pump is activated during respiration, air is pumped through an air pollutant sampling tube. The total volume of air being pumped is displayed in digital readout, as a function of total volume of air being respired. The total volume of air is correlated with the amount of pollutants collected within the air sampling monitor during the given period.

BRIEF DESCRIPTION OF THE DRAWINGS

FIG. 3 is a fragmentary top plan;

FIG. 5 is a fragmentary vertical section of a proposed in-line pumping unit.

DESCRIPTION OF THE PREFERRED EMBODIMENTS

Figure 1:
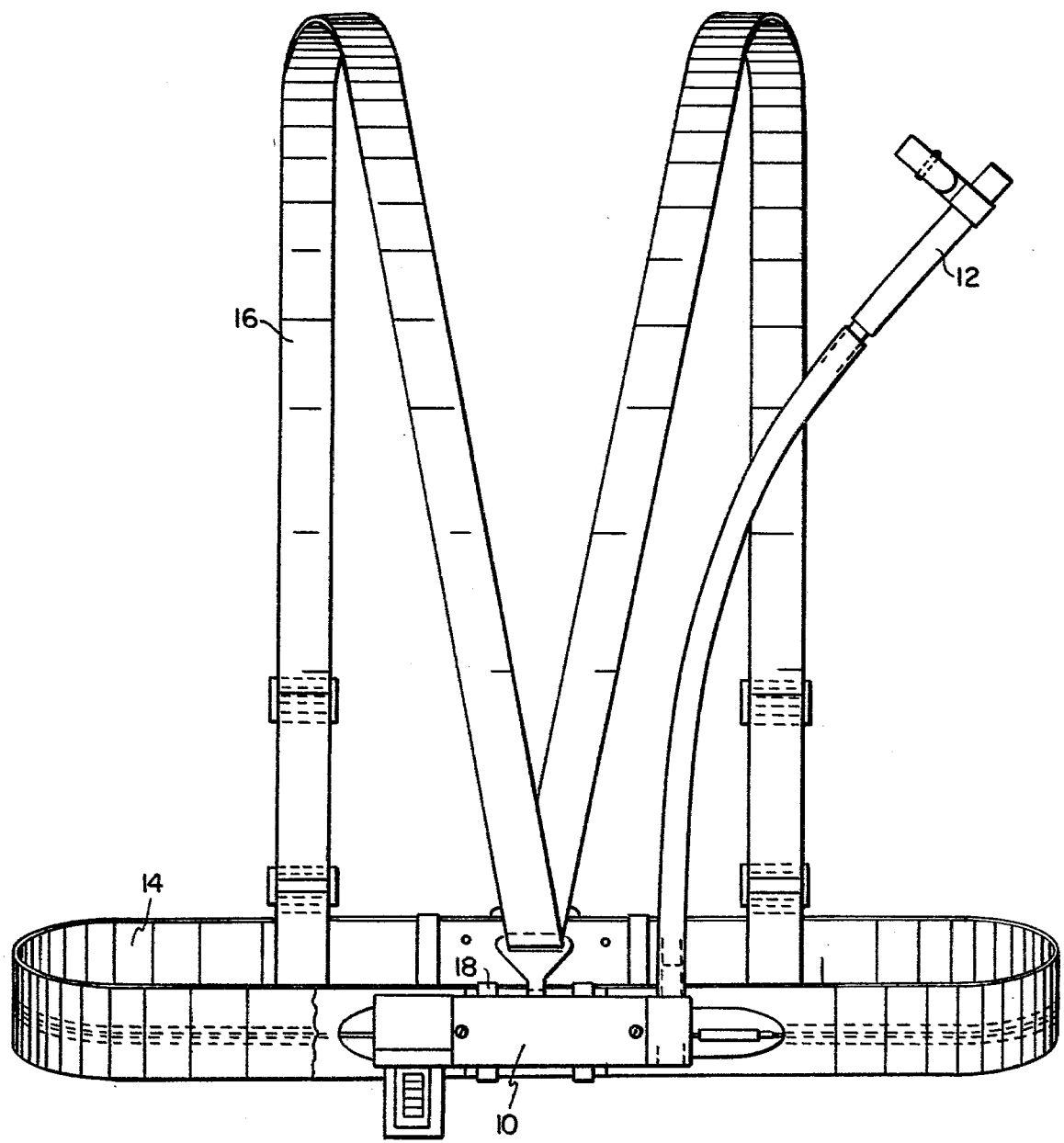
FIG. 1 is a front elevation of a personal monitor harness, secured by an adjustable belt, and supporting an air sampling tube, a pump mechanism and digital readout counter.
Figure 2:
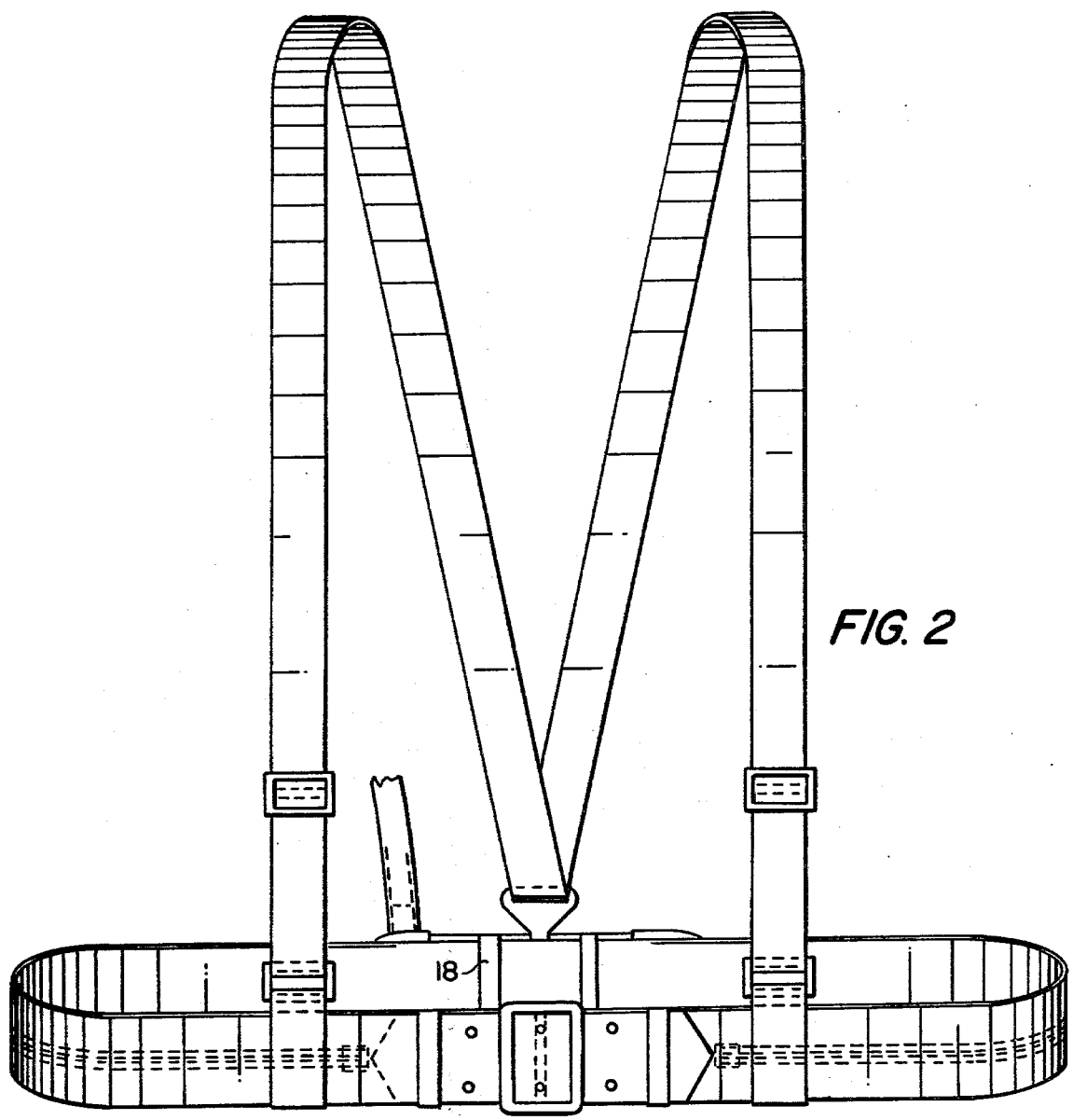
FIG. 2 is a rear elevation thereof.

This sampling system utilizes a conventional cylinder pump positioned parallel to the axis of a supporting belt. FIGS. 1-3 show the concept. Pump 10 and air pollution sampling tube 12 are attached to a belt and shoulder strap 16 harness. The belt 14 in this system is a band of teflon (1.5 inches wide) which reaches around the wearer. Pump 10 which is contained within a cylindrical housing is attached to teflon belt 14 in the front of the wearer. Pump 10 may be fastened to belt 14 by loops 18. A cable 20 is attached at one end to teflon piston 22 and at its other end extends around pulley 30 on the rotating digital counter 26. Cable 20 thus extends from piston fitting 28 to pulley fitting 30. A 0.031 diameter steel cable 60 (7×7 strand) may be mounted within teflon sheath 61 and extend from counter pulley 24 about the torso of the wearer to threaded cable length adjustment coupling 49. Thus at respiration a teflon belt 14 slides about the torso, while cable 20 pulls piston 22 to the left, drawing air and a pollutant into sampling tube 12 and inlet 34.

Entry valve 36 and exhaust valve 42 are located at the right end of piston 22 in alignment with inlet 34. When piston 22 moves to the left during inhalation and expansion of the thoracic cavity, intake poppet valve 36 opens, allowing air to flow into the pump cylinder; this simultaneously draws air through the sampling tube 12, which may contain a conventional silver wool, microfilter or coated lining. When piston 22 passes its position of maximum lateral displacement and is returned, by compression spring 38 as during exhalation, compression within space 40 closes entry valve 36 and opens exhaust valve 42. Both intake valve 36 and exhaust valve 42 are normally closed by compression springs. This situation remains until the position of minimum displacement is reached as piston 22 moves to the right, when the valves are closed until thoracic expansion reopens inlet valve 36. Valves 36 and 42 may be fabricated of light weight rubber balls which seal against rubber O-rings 44 and 46, each valve is returned to its closed position by a weak compression spring.

Figure 4:
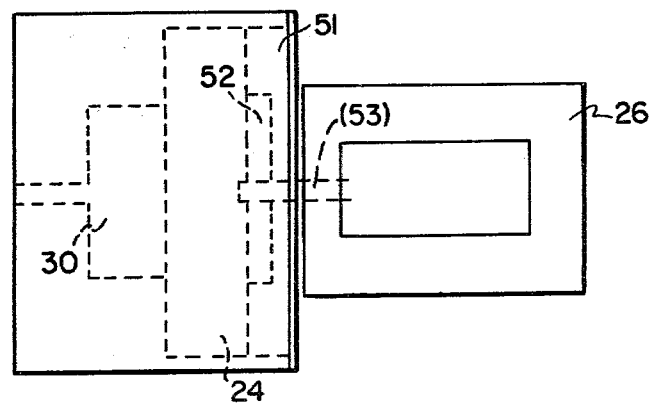
FIG. 4 is a side elevation of the piston clutch and brake components.

As illustrated in FIG. 4, digital counter 26 which records movement in one direction only is a standard revolution counter mounted upon shaft 53 and to which a miniature clutch 51 and brake 52 have been added. Clutch 51 and brake 52 engage counter shaft 53 during the expansion portion of the cycle, as piston 22 moves to the left. No recording of the motion during exhalation is obtained.

Piston 22 which reciprocates in stainless cylinder 47 is fabricated of teflon to reduce friction. Piston 22 may contain an expansion spring in its head in order to maintain the necessary seal. The piston is returned to its minimum position during exhalation by return compression spring 38. Compression spring 38 may be varied to change the sensitivity of the system to small expansions or contractions, as in the case of an infant wearer.

We claim:

1. An in-line respirating pump adapted for support upon the thoracic cavity and comprising:
   (A) An expandable belt including a cable adapted to encircle the thoracic cavity;
   (B) A housing supported horizontally upon said belt, so as to define a horizontal piston chamber and;
      i. a spring-urged piston reciprocally supported in said chamber and connected at one end to said cable, so as to move laterally upon thoracic expansion; and
      ii. an air inlet valve and an air outlet valve defined in said chamber at one end of said piston, each valve being normally biased closed, said inlet valve being openable as said piston moves upon thoracic expansion and said outlet valve being openable, as said piston is returned to closed position as upon exhalation; and (C) An air pollution sampler attached to said inlet valve.

2. A respirating pump adapted for support upon the thoracic cavity as in claim 1, including:
(D) A digital counter supported in said housing and including a rotatable drum supported at one end of said housing connected to said cable.

3. A respirating pump adapted for support upon the thoracic cavity as in claim 2, said digital counter further including a clutch and brake assembly and a digital readout mounted upon a common shaft with said drum, said readout being displayed outwardly of said belt.

4. A respirating pump adapted for support upon the thoracic cavity as in claim 3, said belt including a first cable secured at the valve end of said housing and encircling said belt, so as to be seated within said housing at one end and encircle said rotatable drum at its other end.

5. A respirating pump adapted for support upon the thoracic cavity as in claim 4, said belt further including a second cable at one end encircling a supplemental digital counter drum mounted upon said shaft and at its other end being attached to said piston, such that lateral movement of said piston is effected by rotation of said drum.

6. A respirating pump adapted for support upon the thoracic cavity as in claim 5, said intake valve and said exhaust valve being spring-urged to normally closed position.

7. A respirating pump adapted for support upon the thoracic cavity as in claim 6, including shoulder strap means connectable to said belt, so as to vertically adjust said belt with respect to the thoracic cavity.

8. A respirating pump adapted for support upon the thoracic cavity as in claim 7, said air pollution sampler being positionable upon said shoulder strap, such that the tube opening is adjacent the wearer's mouth.

* * * * *